(12) United States Patent
Hansen

(10) Patent No.: US 6,400,453 B1
(45) Date of Patent: Jun. 4, 2002

(54) INSTRUMENT FOR SELECTING AND DEPOSITING MULTICELLULAR ORGANISMS AND OTHER LARGE OBJECTS

(75) Inventor: W. Peter Hansen, Canaan, NY (US)

(73) Assignee: Union Biometrica, Inc., Somerville, MA (US)

( * ) Notice: Subject to any disclaimer, the term of this patent is extended or adjusted under 35 U.S.C. 154(b) by 0 days.

(21) Appl. No.: 09/378,634

(22) Filed: Aug. 20, 1999

Related U.S. Application Data

(60) Provisional application No. 60/097,505, filed on Aug. 21, 1998, and provisional application No. 60/111,723, filed on Dec. 10, 1998.

(51) Int. Cl.[7] .................................................. B07C 5/36
(52) U.S. Cl. ...................................... 356/237.1; 209/639
(58) Field of Search ................................. 356/237.1, 72, 356/73; 209/639

(56) References Cited

U.S. PATENT DOCUMENTS

| | | | |
|---|---|---|---|
| 3,489,277 A | * | 1/1970 | Silverman ................... 209/639 |
| 5,180,065 A | * | 1/1993 | Touge et al. ................. 209/639 |
| 5,638,961 A | * | 6/1997 | Satake et al. ................ 209/639 |

* cited by examiner

Primary Examiner—Richard A. Rosenberger
(74) Attorney, Agent, or Firm—Stefan J. Kirchanski, Esq.; Crosby, Heafey, Roach & May LLP

(57) ABSTRACT

An instrument for analyzing and dispensing objects larger than about 70 μm in diameter is based on a flow cytometer with a novel fluidic switch arrangement for diverting a portion of a sample stream in response to detector signals in a flow cell. The instrument is particularly adapted for dispensing multicellular test organisms like nematodes or large microspheres for use in screening large libraries of potential pharmaceutical agents. Hydrodynamic focussing is used to center and align the objects in the flow cell. The objects pass through a sensing zone where optical or other characteristics of the objects are detected. The detector signals are processed and used to operate a fluidic switch that is located downstream from the sensing zone. The fluid stream containing the detected objects emerges from the flow cell into air where a fluid stream controlled by the fluidic switch diverts portions of the stream containing no sample objects or sample objects not meeting predetermined characteristics. The undiverted sample stream deposits selected sample objects into a plurality of containers.

56 Claims, 7 Drawing Sheets

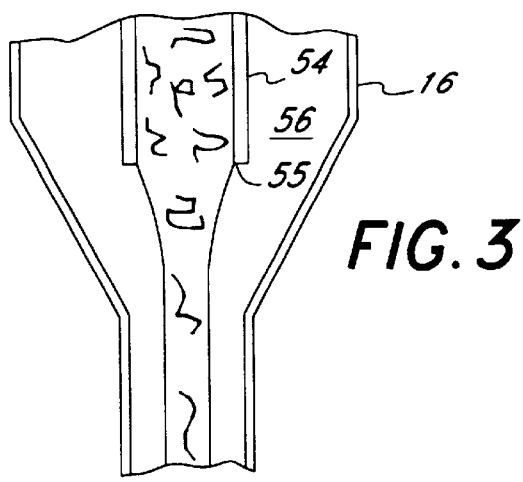
FIG. 3
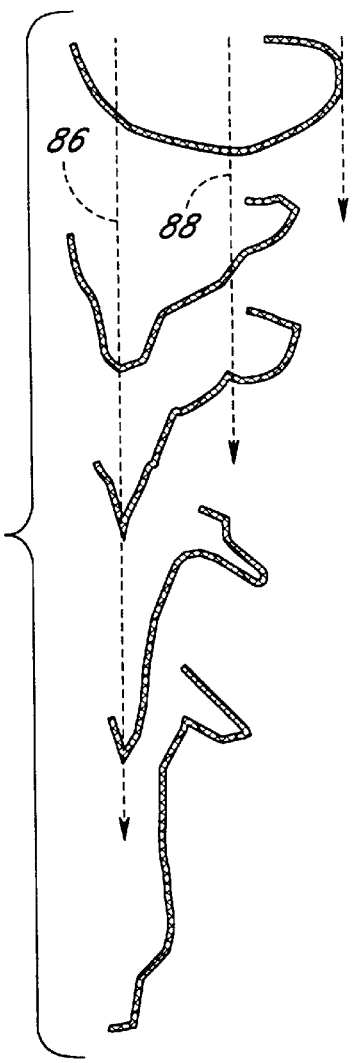
FIG. 4
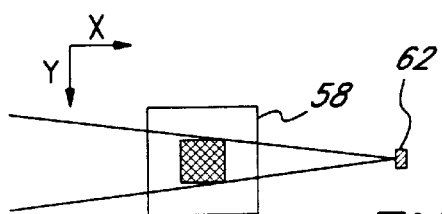
FIG. 5A
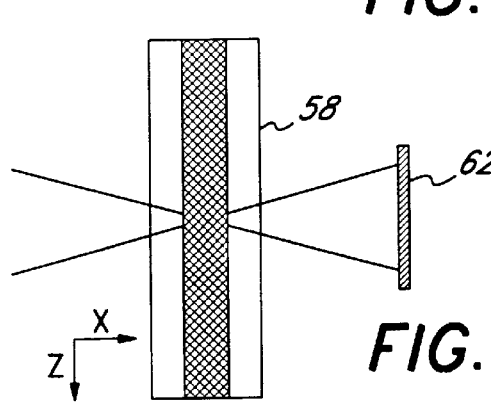
FIG. 5B
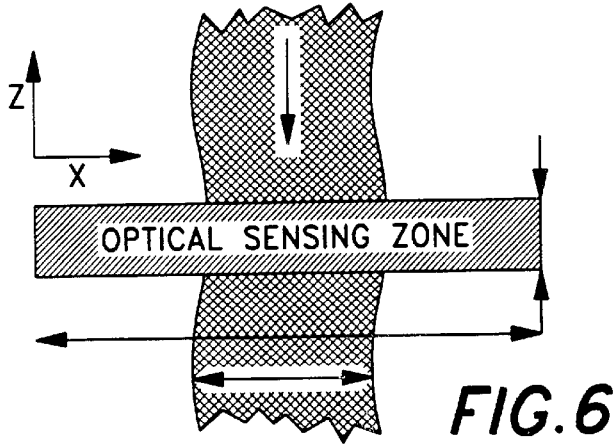
FIG. 6
FIG. 7

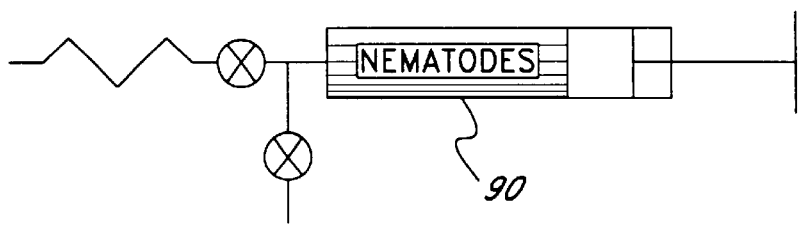
FIG. 8A    FIG. 8B
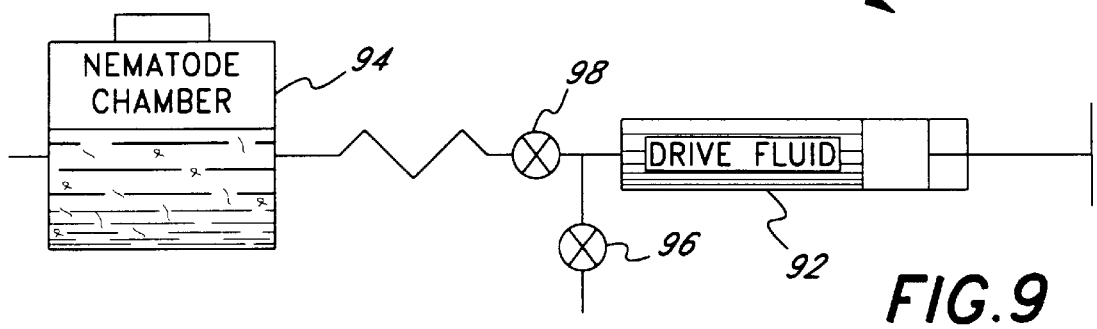
FIG. 9
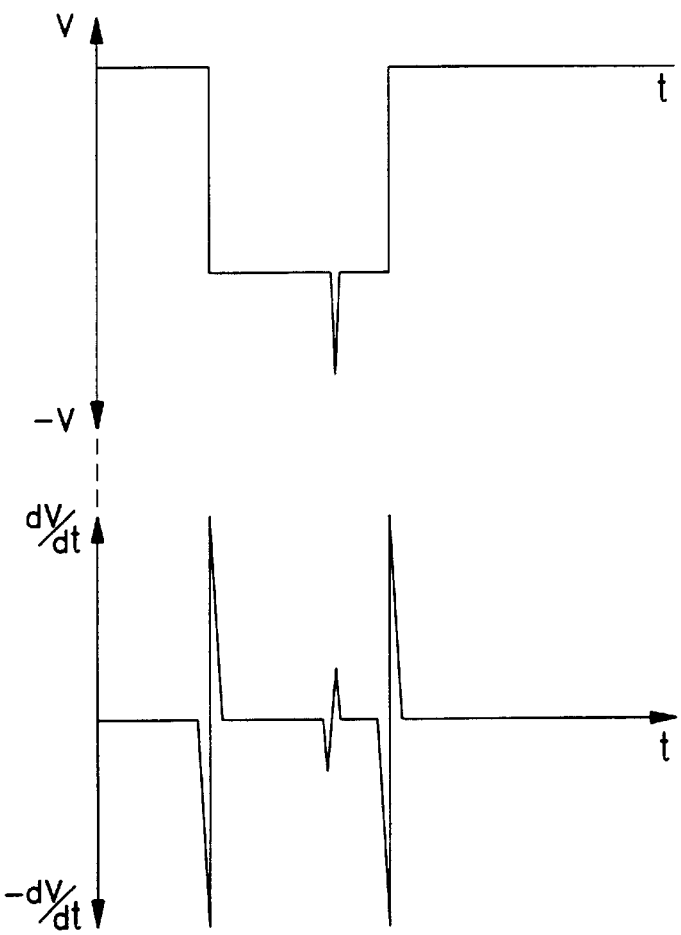
FIG. 10A
FIG. 10B

INSTRUMENT FOR SELECTING AND DEPOSITING MULTICELLULAR ORGANISMS AND OTHER LARGE OBJECTS

The present application is based on U.S. Provisional Patent Application No. 60/097,505 entitled "Fluid Switch Controlled Machine for Selecting and Depositing Multicellular Organisms," filed Aug. 21, 1998 and U.S. Provisional Patent Application No. 60/111,723 entitled "Nematode Sorting Machine," filed Dec. 10, 1998; priority is claimed from these applications both of which are incorporated herein by reference.

BACKGROUND OF THE INVENTION

1. Field of the Invention

The present application concerns high-speed mechanisms for automatically identifying and physically selecting multicellular organisms or other large objects with predetermined characteristics from mixed populations and depositing them in discrete locations.

2. Description of Related Art

Intact multicellular organisms, such as nematodes, fruit fly larvae, or zebrafish embryos are frequently used as model systems to help understand the function of human genes that have been implicated to play a role in disease. Human gene homologous have been identified in these model organisms and mutations have been induced specifically in those gene homologous. Such mutations frequently result in an easily observable phenotypic change in the model organism, and it has been shown that certain mutants respond to pharmacological compounds with a measurable mode of action. Mutants of intact organisms are now used as a new class of in vivo drug screens for combinatorial pharmacological compound libraries. By using these organisms, one can identify targets for drug intervention without the need to completely understand complex biochemical pathways between the genotype and the phenotype. In addition solid state combinatorial chemical approaches are now being utilized to produce these drug libraries; the end result is that the sample chemicals to be tested are present on solid microspheres usually between 100 and 500 $\mu$m in diameter. These solid state techniques greatly speed the preparation of the sample compound library but necessitate a method to accurately select and dispense these microspheres for testing purposes.

The historic approach to modeling diseases in multicellular organisms has been to make morphological or behavioral mutants with substantial phenotypic defects. The intent of such research is to produce a mutant that resembles or models a disease state so that new therapeutics can be screened without using human "guinea pigs." In fact, considering the current prevalence of animal rights activists, the safest approach is to entirely eschew the use of mammals for testing purposes. The goal, then, has been to observe these model disease defects and their interaction with candidate therapeutics objectively and with high sensitivity. Unfortunately, this goal has been not often met. The closest approach to reaching the goal has been to devise "live-dead" assays that can be carried out in microwell arrays using optical readout systems. The plan is to dispense individual organisms into microwells, add the candidate therapeutic and optically detect the response. If the candidate therapeutic is present on a microsphere, then the microsphere must also be accurately selected and dispensed.

The exposure of model organism mutants to diverse pharmaceutical compound libraries, even when the mutation has not been linked to a human gene homologue also helps define gene function. The addition of such functional genomic techniques to the repertoire of molecular biology and biochemistry methods is leading to a significant increase in speed in the pharmaceutical discovery process. Investigators annotate pharmaceutical drug libraries for toxicity, non-specific activity, or cell membrane permeability, etc. by observing their behavior in intact organisms. This way, potential new therapeutics that show toxicity or harmful results can be discarded early without wasting valuable resources.

The soil nematode *Caenorhabditis elegans*, has become a particularly important multicellular organism for these types of tests because its anatomy, development, behavior and genome, is more completely understood than that of any other animal. *C. elegans* is a small metazoan animal composed of only 959 cells, each generated from a single zygote cell through a completely known cell lineage. This small number of cells nonetheless exhibits a diversity of cell types that typifies more complex animals, including skin, muscle, gut and nerve cells.

The genes of *C. elegans* are easily accessed through powerful classical and molecular genetic tools. The sequencing of the *C. elegans* genome is also more advanced than that of any other animal and is a model for the Human Genome Project. Although most human disease genes that have been identified and cloned based on chromosomal position have no known function, the vast majority of these as well as most other human genes have *C. elegans* homologs. These homologs can be rapidly analyzed using the above-mentioned approach to elucidate the functional biology of the homologous human gene.

A striking conclusion from studies of *C. elegans* is that the cellular and molecular mechanisms that operate in this nematode are strikingly similar to those that operate in more complex animals, including man. These similarities are so great that homologous human genes can function in nematodes and nematode genes can function in mammalian cells. Researchers are therefore using this nematode for numerous types of experiments related to the development of pharmaceutical agents for use in humans and other higher animals.

Despite the potential power and speed of using multicellular organisms like *C. elegans* current programs for rapid pharmaceutical drug discovery of not employ high-speed preparation techniques. As an example, with today's molecular biology techniques, a large laboratory can produce deletion mutations in multicellular organisms at a rate of 20 to 30 per month. To evaluate the effect of a chemical compound library (that frequently may contain 100,000 or more members) on a class of mutated organisms, one must first manipulate and deposit a precise number of organisms in the same development stage into a container, such as the wells of a microtiter plate array. Organisms of different development stage must be excluded since they would convolute the measured response.

Using slow, manual methods, the selection and deposition of organisms of the proper type is a bottleneck for the entire process of pharmaceutical discovery. If the test compounds are present as microspheres, then the accurate selection and dispensing of microspheres adds an additional bottleneck. Furthermore, manual methods rely on pipettes that dispense accurate volumes of fluid and not accurate numbers of organisms. In many studies where reproduction rate is altered by the mutation, it is necessary to begin the study of the effect of a compound from the combinatorial library with an exact, and known number of multicellular organisms in each well. Any selection system based on volume is liable to dispense inaccurate numbers of organisms because precisely uniform suspensions of organisms are impossible to maintain. In the same way if the test compounds are available as microspheres it is extremely difficult to place a controlled number of microspheres in each well. Further, the microsphere population may be mixed so ultimate results require not only precise counting but selection of microspheres—clearly an impossible task for simple pipettes.

Flow cytometers have operational characteristics that make them adaptable to the problems of automating the selection and deposition of multicellular organisms and other large objects such as microspheres. Flow cytometers have been used to count the number of nematodes in a given volume of fluid. Such a device was described by Byerly et al (Byerly, L., R. C. Cassada, and R. L. Russell, "Machine for Rapidly Counting and Measuring the Size of Small Nematodes", Rev. Sci. Instrum. Vol 46, No. 5, May 1975) where the flow cytometer utilized sheath flow to orient the nematodes along the direction of flow so that their length could be measured and organism-by-organism counts could be made by an electrical impedance method similar to that used in a commercial Coulter® counter. A flow cytometer for working with multicellular organisms is not limited to using an impedance sensor, biut can be a more modern optically sensing flow cytometer.

For example, an optical flow cytometer for analyzing elongate organisms such as plankton with widths of 500 $\mu$m and lengths over 1000 $\mu$m has been described in a number of published articles such as Peeters, J. C., G. B. Dubelaar, J. Ringelberg, and J. W. Visser, "Optical Plankton Analyser: a Flow Cytometer for Plankton Analysis, I: Design Considerations" Cytometry Sept 10 (5): 522–528 (1989); and Dubelaar, G. B., A. C. Groenwegen, W. Stokdijk, G. J. van den Engh, and J. W. Visser, "Optical Plankton Analyser: a Flow Cytometer for Plankton Analysis, II: Specifications", Cytometry Sept 10 (5): 529–539 (1989). The size range of the plankton used in these optical flow cytometers is similar to that encountered with nematodes, fruit fly larvae, and zebrafish embryos. In all of these references, the multicellular organisms were merely analyzed but were not selected and deposited. Similarly, analysis of large microspheres with flow cytometers is routine as long as the cross-sectional area of the flow cell is sufficient to accommodate the microsphere.

Selection and deposition of non-multicellular organisms and other small objects with flow cytometers is well known. The method used to select and deposit specific organisms or objects (e.g. microspheres) on command from the flow cytometer consists of a mechanism to switch the direction of the flowing stream of organisms or objects that emerges from the flow cell of the flow cytometer so that analyzed objects can be specifically deposited in a microwell plate or similar container. Switching is performed at a fixed delay time after the flow cytometer has identified a desirable organism. The delay is typically in the time scale of a millisecond to tens of milliseconds. The most common method found in commercial cell sorters is electrostatic diversion of desired objects once they have emerged from an exit port in the flow cell into air. Electrostatic diversion is accomplished by charged plates that operate on a stream of droplets.

However, electrostatic cell sorters are designed specifically for single cells and are not useful for sorting large objects such as nematodes, fruit fly larvae, zebrafish or large microspheres. This is because the flow cell of an electrostatic cell is mechanically vibrated at frequencies of tens of kilohertz to mechanically break the fluid stream into (charged or uncharged) droplets in air that are of the order of 50 $\mu$m in diameter. This size droplet is optimal for typical single cells with diameters of 5 $\mu$m to 30 $\mu$m, but it is much smaller than most multicellular organisms, which are typically of the order of 1 mm in length. The mechanical vibration step and the subsequent breakup of the stream into small droplets is typically lethal to multicellular organisms. The vibration frequency of an electrostatic cell sorter is not variable; therefore, one cannot change the droplet size to accommodate multicellular organisms. Furthermore the entire flow cell always vibrates at this frequency, making it impossible to create single droplets on command.

In the case of large microspheres used in combinatorial chemistry there is no worry that mechanical vibration will damage the microsphere. Nevertheless, electrostatic sorters are unable to effectively select and deposit such large objects. This is a result of the geometry used with the electrostatic deflection plates. At the voltages commonly used static charge results in a deviation of only a few degrees. It is impossible to produce greater deviations by increasing the voltages because arching will occur. Adequate deviation to separate selected from rejected droplets is achieved by allowing the stream to fall a sufficient distance beyond the charged plates. In the case of the typical 50 $\mu$m droplet the droplets fall an additional 2.5 cm beyond the deflection plates. If the droplet size is doubled to 100 $\mu$m (still insufficient to accommodate a 100 $\mu$m combinatorial chemistry microsphere), the larger droplet has greatly increased mass which means that the angle of deviation is smaller; therefore, a longer fall distance is necessary to produce adequate deflection (i.e., the deflection angle is smaller). The net result is that 100 $\mu$m droplets require a fall distance of 20 cm. With such a large fall distance tiny instabilities in the flow stream are magnified into appreciable deflections. The microwells of the plates in current use may be on the order of one to a few millimeters in diameter. With a 20 cm fall distance current electrostatic sorters are unable to accurately hit such a small target. The problem becomes even more acute when the droplet size is increased farther to accommodate 400 $\mu$m microspheres or multicellular organisms. With a droplet size of one-millimeter (the size necessary to cushion a typical nematode) the fall distance increases to about 125 cm making it totally impossible to deposit droplets in target containers of even several millimeters diameter.

Thus, electrostatic sorters are completely unsuited to multicellular organisms or other large objects. Even if the process does not kill or damage the organism, the deflection geometry makes it impossible to accurately deposit large objects.

SUMMARY OF THE INVENTION

The invention features an instrument for selecting and accurately dispensing multicellular organisms and other large objects. The instrument uses hydrodynamic flow conditions in an alignment chamber to align elongate multicellular sample organisms and center organisms or objects in the center of a fluid flow stream after which they pass single file through a sensing zone which is preferentially within the chamber. In the sensing zone the aligned and centered objects are interrogated preferably by a light beam. Optical detectors receive refracted, reflected, fluoresced and scattered light from the interrogated objects and output corresponding electrical signals. A signal processing computer system uses these signals to choose desired analyzed objects. A first fluid switch downstream of the sensing zone and outside of the chamber is responsive to signals developed by the computer system. When the switch is open, the flow stream containing the objects passes the switch and into a collection container. When the switch is closed, a fluid stream from the switch deflects the flow stream containing the analyzed objects and prevents it from reaching the collection container.

In preferred embodiments, the fluid switch can include a switched source of compressed gas having a gas output directed toward a location downstream from the sensing zone and outside of the chamber. The switched source of compressed gas can include a source of compressed gas and an electrically operated valve, such as a solenoid valve, to interrupt a gas stream from the source of compressed gas. The switched source of compressed gas can be operative to interact with the fluid flow stream carrying objects from the sensing zone with sufficient force to convert the carrier fluid into a droplet spray. A sample source can be operative to supply a fluid carrying a sufficiently low concentration of large sample objects that the objects flow substantially one at a time through the sensing zone. The fluid switch can be responsive to a delayed detection signal from the computer system. The fluid switch can be operative to include only predetermined amounts of fluid with the selected sample object. The computer system can be operative to cause the switch to select one object at a time, with each object being accompanied by a predetermined volume of fluid.

An illumination source can be directed toward the sensing zone, with the detector being an optical detector. The computer system can be operative to determine the length of at least one of the selected objects by measuring the time that the at least one of the objects takes to pass between the detector and the illumination source. The detector can be an on-axis detector, located across the sensing zone along an illumination axis of the illumination source. The detector can be an off-axis detector generally perpendicular to an illumination axis of the illumination source. An on-axis detector can be located across the sensing zone along the illumination axis of the illumination source. The illumination source can be a focused low-power laser. The sensing zone can have a width of about 10–40 $\mu$m. The sensing zone can have a square cross-section. The output opening of the sample source can be separated from the sensing zone by a total conduit volume of less than 500 microliters. A second fluid switch downstream of the first fluid switch and outside of the chamber can dispense the selected objects into different containers.

In another general aspect, the invention features a multicellular organism or large particle dispensing instrument that includes means for aligning the organisms or objects in a fluid stream in a direction parallel to a flow direction of the fluid stream, means for detecting the presence of the organisms or objects in the fluid stream located downstream from the means for aligning, and means for selectively diverting portions of the fluid, with the means for selectively diverting being located downstream from the means for detecting, being outside of any chamber containing the means for aligning and being responsive to the means for detecting.

In preferred embodiments, the multicellular organism and large object dispensing instrument can further include means for redirecting an output of the means for determining relative to a first container to thereby dispense further ones of the organisms into a second container. The means for selectively diverting can be for including only a predetermined amount of fluid with each of the organisms selected.

In a further general aspect, the invention features a method of dispensing multicellular organisms and large objects that includes centering and orienting the organisms or objects in a longitudinal orientation in a chamber, flowing the organisms in the longitudinal orientation through the center of a sensing zone with a carrier fluid, and detecting the presence of the organisms or objects in the sensing zone. At least some of the carrier fluid is diverted by means for diversion based on the step of detecting ones of the organisms or objects and ones of the organisms or objects remaining in portions of the carrier fluid that were not diverted are collected. The means for diversion are disposed outside of the chamber.

In preferred embodiments, the step of diverting can include a step of converting the carrier fluid into a droplet spray. The step of diverting can take place for a predetermined period of time for each of the detected organisms. The method can also include step of illuminating the sensing zone, with the step of detecting light from the step of illuminating. The step of detecting can employ an on-axis detector and an off-axis detector and combine signals from these detectors. The step of centering can include a step of conveying a sheath fluid past a nozzle. The step of conveying can be performed with a maximum Reynolds number of around one hundred. The method can further include a step of sorting the organisms or objects into a plurality of categories after the step of diverting, with the step of collecting placing the organisms or objects in a plurality of different containers. The method can further include the step of exposing the organisms collected in the step of collecting to a pharmaceutical agent, which may be borne by a large object. The step of dispensing the organisms can include dispensing predetermined numbers of nematodes into each of a number of containers. The step of flowing can introduce reference particles along with the nematodes. The step of dispensing can include dispensing only multicellular organisms having a particular characteristic into a given container.

In another general aspect, the invention features a dispensing instrument that includes a source of organisms or large objects, a sensing zone responsive to presence of organisms or objects, a detector directed toward the sensing zone, and a first switched source of fluid having an output directed toward a location downstream from the detector and having a control input responsive to the detector.

In preferred embodiments, the switched source of fluid can include a source of compressed gas and an electrically operated valve, such as a solenoid valve, to interrupt a gas stream from the source of compressed gas. The switched source of fluid can be operative to interact with a fluid stream from the detector with sufficient force to convert fluid in the detector fluid stream into a droplet spray. The switched source of fluid is not contained within any flow chamber so as not to introduce fluidic instabilities. The switched source of fluid can be responsive to a delayed detection signal from the detector. The dispensing fluid switch can be operative to repeatedly leave predetermined amounts of detector fluid stream fluid undiverted. The dispensing instrument can further include a second switched source of fluid positioned to divert fluid left undiverted by the first switched source of fluid.

In a further general aspect, the invention features a dispensing instrument that includes means for providing a fluid stream carrying objects, the means for providing being located within a flow chamber, means for detecting the presence of the objects in the fluid stream, the means for detecting being located downstream from the means for providing, and first means for selectively directing a gas stream toward the fluid stream to divert portions of the fluid, the means for selectively directing being located downstream from the means for detecting, outside of the chamber, and being responsive to the means for detecting.

In preferred embodiments, a second means can be provided for selectively directing an output of the first means for selectively directing, relative to a first container to thereby dispense portions of the fluid stream into a second container. The means for selectively diverting can be for including only a predetermined amount of fluid with each of the objects selected.

In another general aspect, the invention features a dispensing method that includes feeding objects through the center of a sensing zone with a carrier fluid, detecting the presence of the objects, diverting at least some of the carrier fluid based on the step of detecting, and collecting ones of the objects remaining in portions of the carrier fluid.

In preferred embodiments, the step of diverting can include a step of converting the carrier fluid into a droplet spray. The step of diverting can take place for a predetermined period of time for each of the objects. The step of diverting is physically removed from the step of detecting so as to avoid introducing fluidic instability. The method can further include a step of sorting the objects into a plurality of categories after the step of diverting and the step of collecting can collect the objects in a plurality of different containers. The method can further include the step of exposing the objects collected in the step of collecting to a pharmaceutical agent. The step of dispensing the objects can include dispensing predetermined numbers of the objects into each of a number of containers. The step of feeding can feed reference particles with the objects. The step of dispensing can include dispensing only objects having a particular characteristic into a container.

Systems according to the invention can help to accelerate and reduce the cost of pharmaceutical development. By rapidly sorting and depositing large numbers of live populations with particular characteristics, a sorting instrument according to the invention can allow many compounds to be tested on the sorted organisms in a given time period. By permitting particular types of multicellular organisms to be selected from large populations, individuals with infrequent mutations can be collected and studied more quickly. By permitting the selection and accurate deposition of large microspheres bearing test compounds the test organisms and test compounds can be rapidly and accurately combined. As a result, more experiments can be performed in the same amount of time, and these experiments can be performed at a lesser expense.

BRIEF DESCRIPTION OF THE DRAWINGS

FIG. 3 is a diagrammatic cross-section of a flow cell for use in the system of FIG. 2;

FIG. 4 is a diagram illustrating the alignment of elongate sample organisms in the sheath flow cell of FIG. 3;

FIG. 5A is an axial cross-section of a sensing chamber of a flow cell and detector for the system of FIG. 2;

FIG. 5B is a longitudinal cross-section of the sensing zone of the flow cell and detector for the system of FIG. 2;

FIG. 6 is a longitudinal cross-sectional diagram illustrating the relationship between a nematode and an optical sensing zone of a sheath flow cell for the system of FIG. 2;

FIG. 7 is diagrammatic plot of voltage against time for a light blocking signal in the system of FIG. 2;

FIG. 8A is a block diagram of a first alternative fluid drive system for the system of FIG. 2;

FIG. 8B is a cross-sectional diagram of a syringe for the system of FIG., 8A;

FIG. 9 is a block diagram of a second alternative fluid drive system for the system of FIG. 2;

FIG. 10A is a diagrammatic plot of voltage against time for a light blockage signal produced by an adult nematode and a coincident egg;

FIG. 10B is a diagrammatic plot of the derivative of the signal of FIG. 10A;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a device for selecting and depositing elongate multicellular organisms or other large objects using a high speed fluidic switch and controlled fluid stream to deflect unselected organisms.

This application refers repeatedly to large objects and multicellular organisms. By "large" is meant objects or organisms significantly larger than those analyzed and sorted by a traditional electrostatic sorter which normally sorts objects on the order of 10 $\mu$m diameter with droplets on the order of 50 $\mu$m diameter. Large objects are larger than 50 $\mu$m diameter and preferably have at least one dimension ranging between 70 and 500 $\mu$m or larger. The droplet sizes employed with the current invention are at least 100 $\mu$m in diameter and preferably 1 mm in diameter. Thus, "large" objects are at least one order of magnitude larger than those handled by traditional electrostatic sorters.

Figure 1:
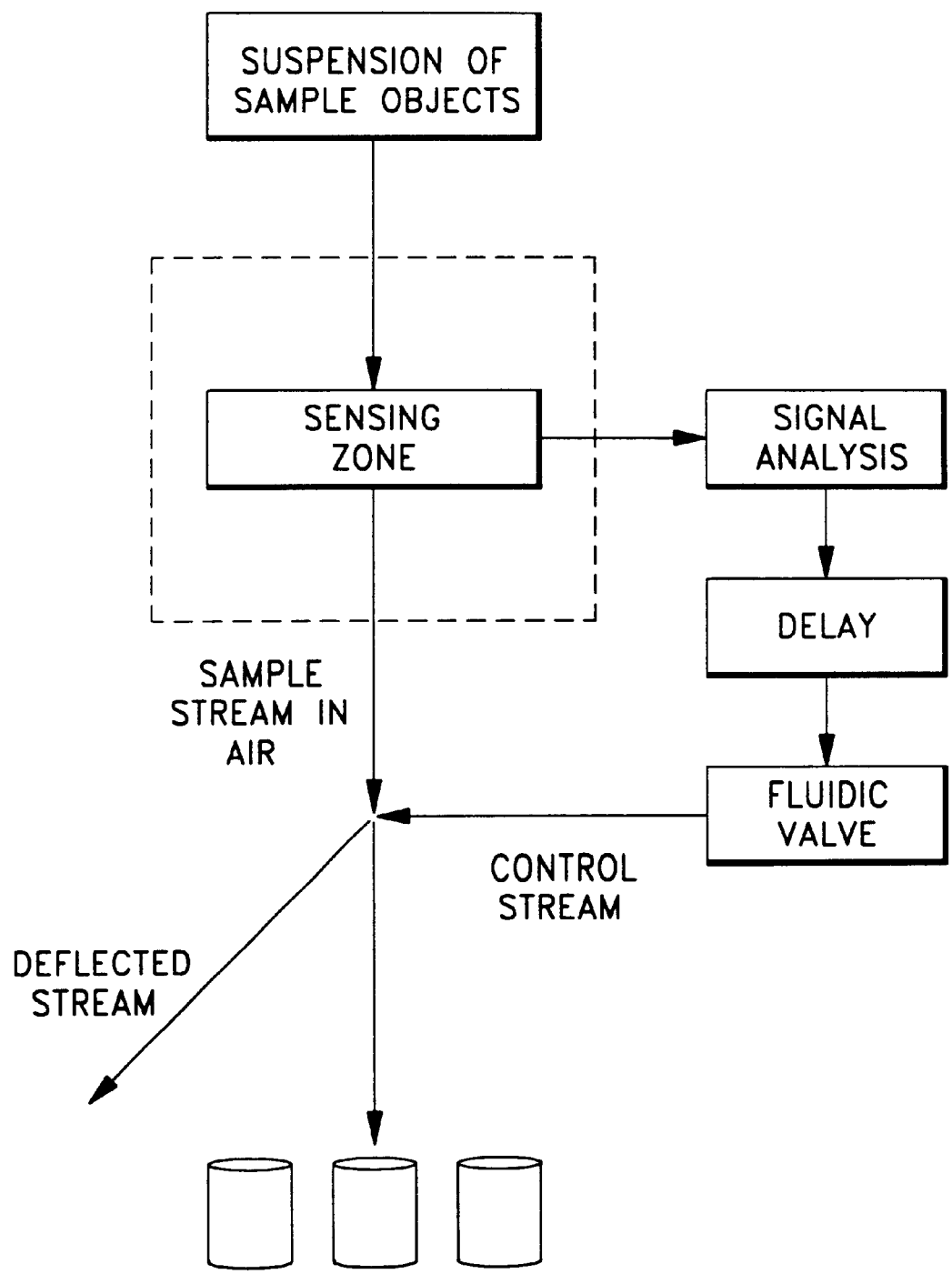
FIG. 1 is a general diagrammatic sketch of the analysis and dispensing system of the present invention.

FIG. 1 shows an extremely diagrammatic representation of the instrument of the present invention. Attention should be paid to the salient elements of the present invention. Large sample objects from a source 46 are centered and aligned in a fluid stream in a flow chamber 16 by hydrodynamic focussing. Detectors detect characteristics of sample objects in the flow stream. Down stream from the detectors and physically isolated from the detectors to avoid propagation of fluidic instabilities a control stream of fluid under the control of an electronic valve 20 diverts portions of the sample stream not desired. Sample stream portions containing sample objects meeting predetermined characteristics are not diverted and pass into one of a plurality of indexable containers 82.

Figure 2A:
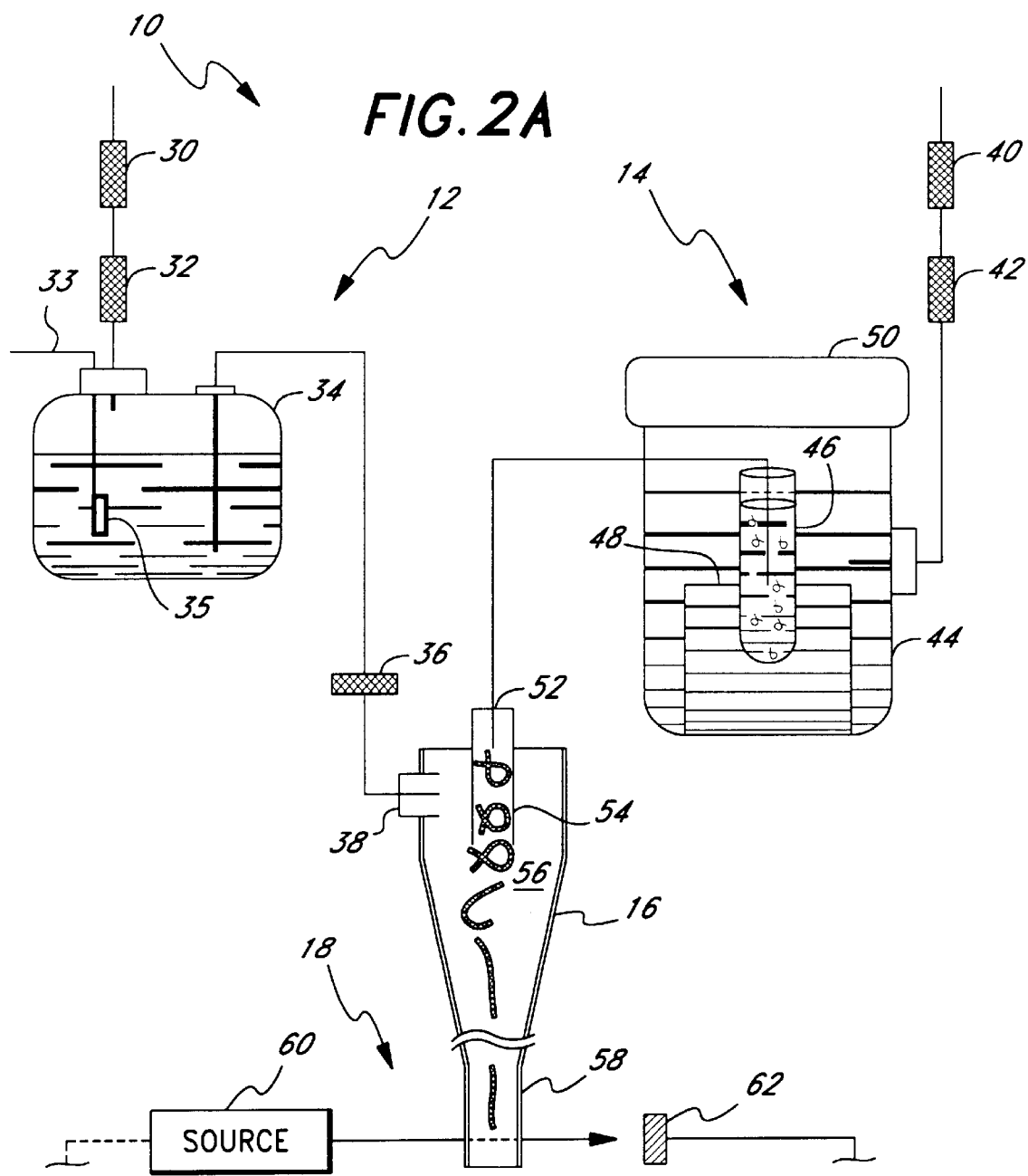
FIG. 2 is a block diagram of a large object dispensing system according to the invention.
Figure 2B:
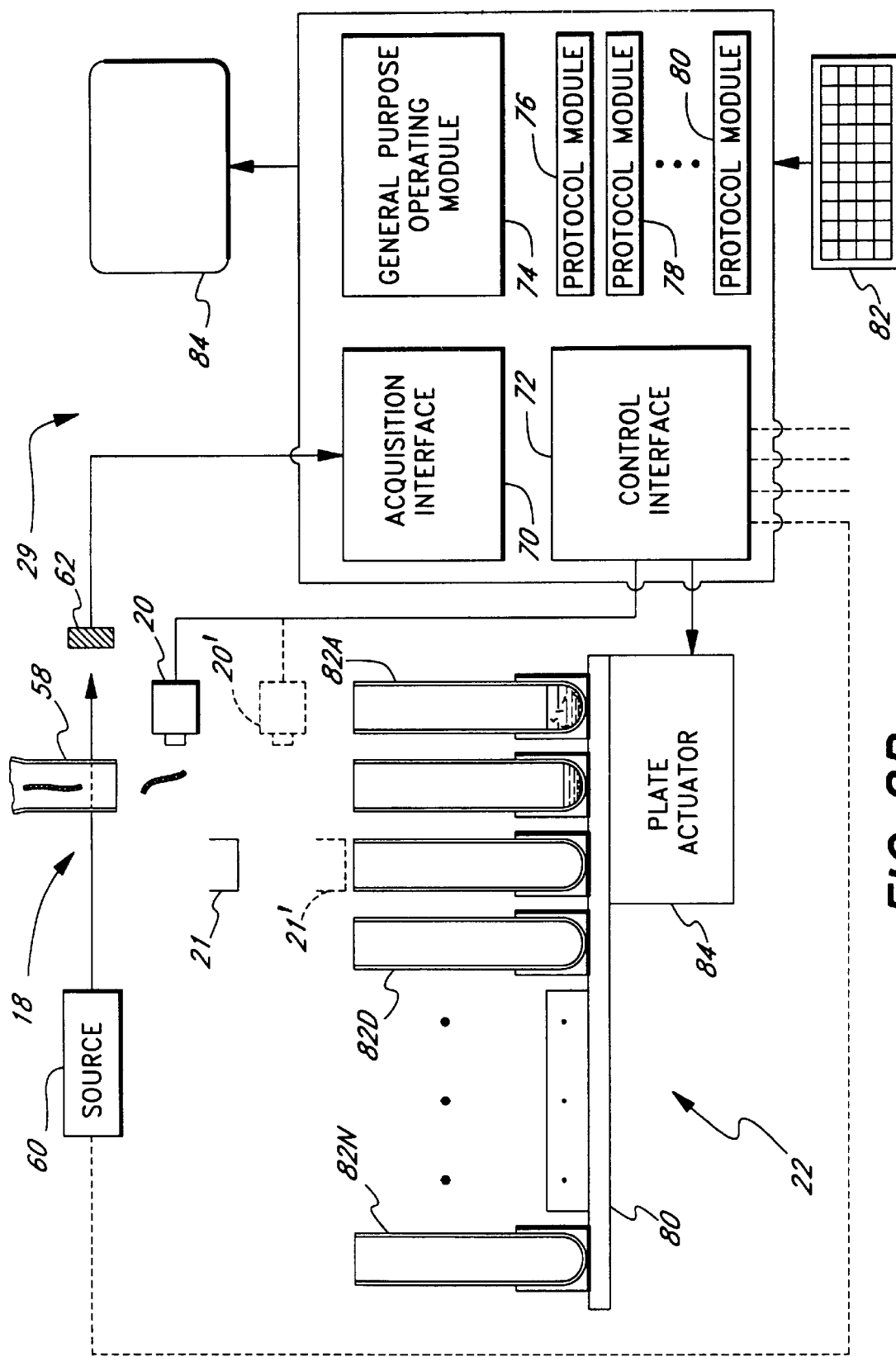

Referring to FIG. 2, a dispensing system 10 for elongate, multicellular, invertebrate animals, such as nematodes, or for other large objects includes a sheath fluid drive system 12, a nematode fluid drive system 14, a sheath flow cell 16, a detection system 18, a sorting actuator 20, a container actuation system 22, and a diagnostic and control processor 24. The sheath fluid drive system includes a first stage regulator 30 that has an input opening for a pressurized gas source, such as a 25–30 psig nitrogen or a compressed air source. A second stage regulator has an input connected to the first stage regulator and an output delivering gas at a regulated pressure to a sheath fluid reservoir 34. An electronic level sensor 35 controls a sheath fluid input line 33 to maintain a constant level in the reservoir. A particle filter 36 is connected between an output of the sheath fluid reservoir and an input opening 38 of the flow cell to prevent any particles in the sheath fluid from passing into the flow cell.

A sample fluid drive system similarly includes a first stage regulator 40 connected to a pressurized gas source, such as a 25–30 psig pressurized nitrogen or air source. A second stage regulator 42 is connected between the first stage regulator 40 and an input of a sample pressure vessel 44, which is sealed with a clamped cap 50. The sample pressure vessel 44 includes a sample storage reservoir 46 mounted on a mixing device 48. The multicellular sample organisms such as nematodes are placed into the sample storage reservoir 46. The mixing device 48 can be a magnetic stirrer that includes blades that produce an upwelling in the fluid containing the suspended sample organisms or objects. An outflow line is provided between the sample storage reservoir 46 and a sample feed input 52 of the flow cell 16. The flow cell 16 includes a sample feed chamber 54, a sheath fluid chamber 56, and a sensing chamber 58. To operate effectively in commercial settings, the dead volume in the outflow line and flow cell should be low, such as less than 500 microlitres.

The detection subsystem 18 includes a source 60 and a detector 62 placed on either side of the sensing chamber 58. The source can be an optical source, such as a laser (e.g., a semiconductor laser or a helium-neon (HeNe) laser). The source can also be a non-optical source, or it can even be omitted, such as when chemiluminescent, phosphorescent or radioactive markers are used on the organisms or objects themselves. The preferred embodiment uses an optical detector but may be readily supplemented with an additional detector for non-optical radiation, magnetism or other physical properties that may distinguish organisms or other analyzed objects. An optical detector can be a photodiode, or any other suitable type of optical or non-optical detector. A second, off-axis detector can also be provided, such as to detect light scattered from the sensing chamber at right angles. The off-axis detector is located generally perpendicular to an illumination axis of the source.

The sorting actuator 20 can be a switched source of fluid. An example would be a high-speed valve that switches air from a pressurized air source. High-speed valves made for ink-jet printing applications have appropriate characteristics. Suitable valves of this type include the Inka series (e.g., INKA4004212H) miniature solenoid valves, available from the Lee Company of Westbrook, Conn. These valves can operate from a low voltage source at rates of up to 1200 Hz, easily allowing the system to handle rates of 50 sample organisms per second or better, although rates of 10 or 20 organisms per second are relatively satisfactory for dispensing into 96-well plates. An extremely important aspect of the current invention is the placement of the actuator 20. The objects to be analyzed and deposited are oriented and preferably detected within a flow chamber; the actuator 20 must be placed down stream and outside of this flow chamber so that the diversion process is physically isolated from the chamber. Otherwise fluidic disturbances introduced by the diversion process would prevent analysis and selection of large objects at any reasonably high speed.

A gutter 21 is placed across from the actuator in such a way as to catch animals or objects that are deflected when the actuator is in its open state. In summary when the actuator is closed, the sample stream containing the sample organisms passes through the flow cell and into the collection container such as a microwell of a microtiter plate. When the actuator is open, the sample stream is diverted in the gutter 21 and does not reach the microwell. Clearly, such a deflection process operates optimally when the deflection occurs outside of and away from the flow chamber.

The container actuation system 22 includes a plate 80 (e.g., a microtiter plate) that includes a plurality of containers 82A . . . 82N (e.g., microwells) into which the system dispenses the sample organisms. The plate is mounted on a plate actuator 84 that includes a drive mechanism. The drive mechanism successively places the containers of the plate in the outflow path of the flow cell 16. The drive mechanism is under control of the diagnostic and control processor 24.

The diagnostic and control processor 24 includes an acquisition interface 70 having an input responsive to the detector 62. It also includes a general-purpose operating module, and one or more protocol modules 76, 78, 80. A keyboard 82 (or similar data input means) is operationally connected to the computing system that also drives a display 84. The diagnostic and control processor 24 also includes a control interface 72 that can provide an actuator control signal to the actuator 20 and a source control signal to control the source 60.

The diagnostic and control processor 24 can include dedicated hardware, special-purpose software running on a general-purpose computer processor, or a combination of the two. The decision to implement any specific functionality using a particular approach will be based on a number of economic and technical considerations and tradeoffs. For example, the acquisition interface 70 can filter and condition the signal received from the detector 62 using either analog circuitry or software signal processing routines or a hardware DSP (digital signal processor). The objectives of the system may also be met by variants of the architecture shown. For example, the plate actuator might be controlled by a controller that is independent of the diagnostic and control processor, such as a dedicated fill-level detector. Changes may also be made to the hydraulic portions of the system without impacting its functionality or objectives as long as certain points are observed: the fluidic diversion process must be physically isolated from the orientation and detection processes. An optimal method of achieving this isolation is to place the fluidic diversion downstream and outside of the flow chamber where the fluidic diversion operates on a sample stream in air. This makes it impossible for fluidic instabilities caused by the diversion process to be transmitted upstream into the detection zone where they would disrupt the entire process.

Figure 11:
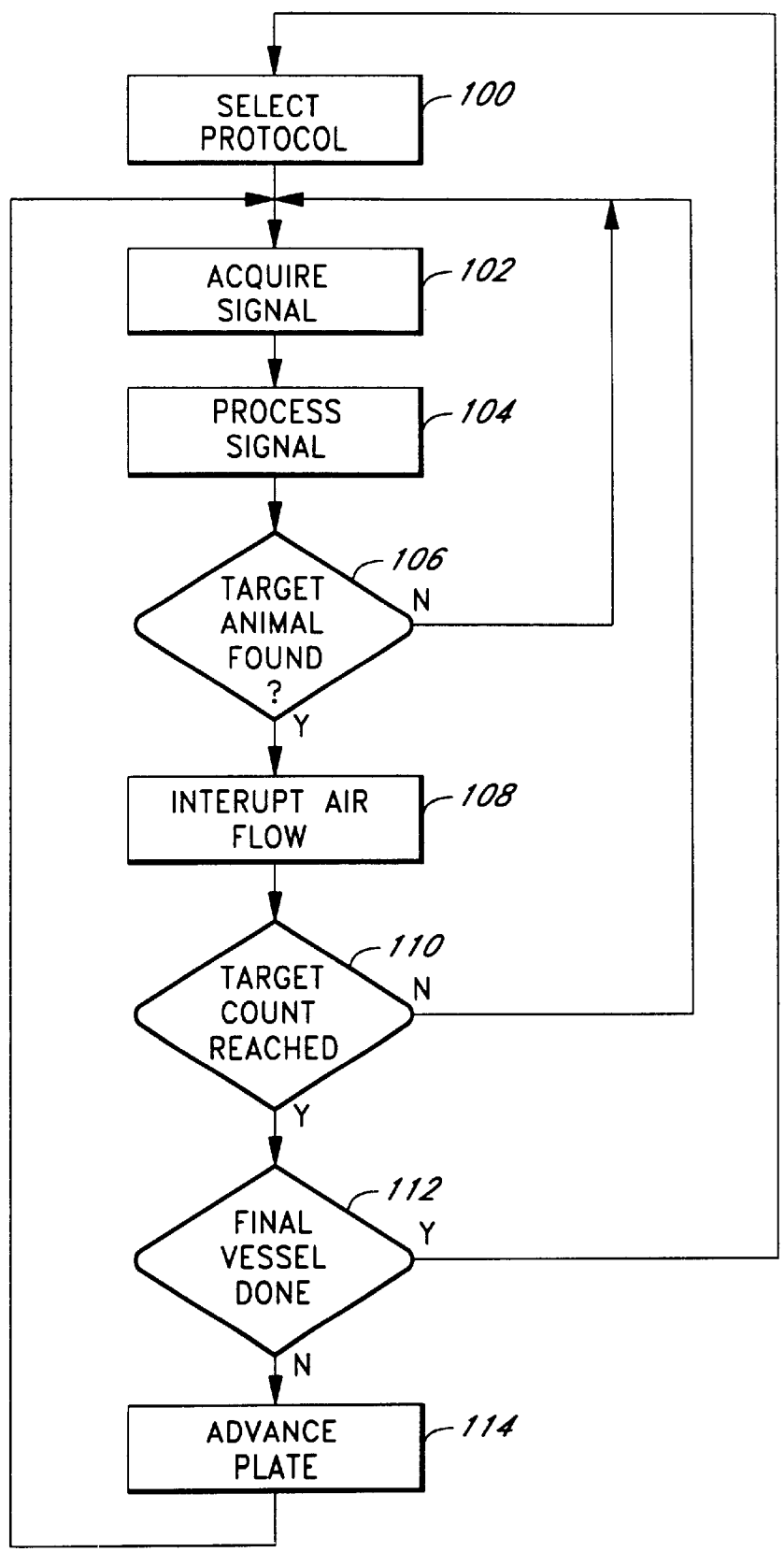
FIG. 11 is a flow chart illustrating the overall operation of the system of FIG. 1.

Referring to FIGS. 2 and 11, operation of the system 10 begins with user selection of a protocol for a particular dispensing operation (step 100). This can be accomplished by calling one of the protocol modules 76, 78, 80, which handle different types of operations. For example, a simple counting module allows the system to dispense a fixed number of sample organisms into each of the containers 82A . . . 82N. A more sophisticated counting operation may count the organisms while eliminating undesirable material such as eggs, etc. Even more elaborate protocols can detect the characteristics of individual organism or particles and only select those with particular developmental, genetic or other characteristics, such as by detecting a radioactive or fluorescent marker on the organism or particle or by detecting a particular size or shape of the object. Still more complex protocols allow parts of the system to sort objects into two or more subpopulations, while also rejecting undesirable material (e.g., organisms of the wrong stage or type or debris or particles of the wrong size, etc.).

The first step specified by the protocol is to acquire from the detector 62 a signal that represents the interaction between light from the source 60 and sample objects in the sensing chamber 58, when an optical detection scheme is employed (step 102). The diagnostic and control processor 24 then performs signal processing operations, such as filtering, on the acquired signal to enhance the detection of sample object (step 104). The computer system tests the processed signal for a detection condition, until a target object is found (step 106). The detection condition may be different for different protocols. For example, the computer system may only seek animals without coincident eggs, or other debris. Alternatively, it may require that a sample organism or particle meet particular size or shape criteria.

Different types of detectors may also be associated with different detection conditions. For example, a radiation counter may need to sense a radiation level threshold to detect a radioactive marker in an animal. A magnetic sensor may detect magnetic particles used in combinatorial chemistry. Alternatively, an optical detector may need to sense a particular level of light to detect a bioluminescent, chemiluminescent, phosphorescent or fluorescent marker. When the computer finds a target object that meets the proper criteria, the valve of the sorting actuator 20 interrupts the gas flow that is directed at the sample stream exiting the flow cell 16 (step 108) for a predetermined period of time corresponding to the target object's length. This prevents the target object from being accidentally blown into the gutter 21. If this is not the last object needed in a particular container, the system continues to acquire, process, and test the signals either until another target object is detected, until a timer expires, or until an error signal is encountered (step 110). When the system reaches the target count for the container, and other containers remain to be filled (step 112), the control interface 72 of the computer system 24 instructs the plate actuator 84 to advance the plate 80 (step 114). After the plate has been advanced, the signal is again acquired, processed, and tested to select objects to dispense into the next container.

More complex protocols can operate a pair of sorting actuators, 20', or a multi-level actuator, to direct target objects to three or more destinations, such as either a vessel, a first gutter 21, or a second gutter 21' placed downstream from the first gutter 21 (see dashed lines in FIG. 1). In this type of configuration, the system can readily separate a population of sample objects into two subpopulations, while also rejecting undesirable material. Again, both sorting actuators are down stream from and outside of the flow chamber so that the sorting process cannot introduce fluidic instabilities.

Referring to FIGS. 3 and 4, the flow cell 16 is constructed to center and align the elongate sample organisms in the detection chamber. Differing velocities within the fluid in the flow cell cause the organisms to become aligned with the flow direction. This happens because fluid flowing further from the center of the cell (e.g. 86) moves at a faster rate than fluid flowing closer to the center of the cell 87 (e.g. fluid along line 88). This velocity difference causes the organisms to become aligned in almost all instances. Although occasional folding of the sample organisms may occur, such organisms can be rejected by the sorting mechanism.

The aligning effect of the flow cell 16 can be pictured by imagining a strand of limp spaghetti being moved through water by an intersecting smooth rod. The spaghetti will virtually always straighten out and slip off the rod because of the unbalanced drag on the longer end of the strand. The only case where this does not occur is when the rod is exactly in the middle of the strand.

The flow cell 16 is configured to cause the sheath flow liquid to flow past the opening of the sample organism feed tube 54 at a rate that maintains the Reynolds number of the sheath fluid below about one hundred. Keeping the Reynolds number below about one hundred ensures that the flow is laminar and without Van Karman instability, which helps to keep the sample organisms centered in the sensing chamber. The Reynolds number is computed by treating the edge 55 of the opening of the sample flow tube 54 as a bluff object. The hydrodynamics of bluff objects are discussed in, for example, sections 9.1–9.2 of "Principles of Heat Transfer," by Frank Kreith, International Textbook Company, Scranton, Pa. 1966, which is incorporated herein by reference.

It is important to center the sample organisms in the flow stream because the velocity of the fluid is not the same across the diameter of the sensing chamber 58. Since fluid viscosity, density, and velocity used in the system are selected to give rise to laminar flow, the velocity profile is parabolic in the detection cell. This means that the velocity is a maximum and roughly constant over a reasonably broad region of the center of the cell, and is zero at the boundary between the fluid and the cell wall. As a result, centered sample organisms will all flow at a single velocity and not pass one another or "bunch" together. If the organisms were not centered, those near the wall could flow more slowly than those at the center, which could result in "coincidence counting"(e.g., more than a single organism at a time passing the sensing zone) even when the dilution of organisms in the sample organism chamber has been calculated to avoid such coincidence. Lack of centering could also mean that, after detection, an organism near the wall might travel so slowly that other organisms could pass it, enter the fluid space that was reserved for the slower organism, and be incorrectly dispensed. There is essentially no mixing of the sample fluid with the sheath fluid until the two are dispensed into the container.

Referring to FIGS. 5A, 5B, and 6, the sensing chamber 58 has a square cross-section. This shape makes the cell easy to align optically, and it should stay in proper alignment for months without operator intervention. The shape of the beam in the focal region, or "sensing zone," is extremely important. The beam should be broad in the x direction, (i.e., along the beam) and narrow in the z direction (i.e., along the horizontal axis). From the standpoint of optical kinematic design, the only difficult alignment direction in the system is in the x direction, which is why a broad, forgiving beam is used in this dimension. A sharp focus (FIG. 5B) in the z dimension permits the system to measure a sample organism along its axis (length) by measuring its "time of flight" through the sensing zone. In one embodiment, optimized for organisms approximately 70 $\mu$m in diameter, the optical sensing zone is 20 $\mu$m thick in the z direction, and the sensing chamber is 300 $\mu$m wide in the x and y directions. The relative positions of the source 60, the sensing chamber 58, and the detector 62 cause the detector to measure light blockage. When a sample organism passes into the sensing zone, some light will be scattered out of the beam (major effect), while some light will be absorbed (minor effect). Both of these effects cooperate to lower the light level at the detector when an organism passes through the sensing chamber. The drop in the light passing from the source to the detector can be readily registered as a count by an electronic threshold detector, and passed onto the processor 24, or even to a less sophisticated device, such as a counter. Noise generated in the laser and the detector should not be a consideration in the detection of objects as large as multicellular sample organisms.

The system can use detector pulses to simply count and activate a dispensing command, but pulses can also be used to size the sample organism. Sizing is not quantitatively essential in a sample population that has been purified by a gradient, but it is nevertheless important to set a size threshold to separate background debris from the target organisms. The presence of an object is sensed by a drop in voltage from the detector, which persists as long as the object is in the sensing zone (see FIG. 7 where the width 93 of the detected pulse 91 is representational of organism dwell time in the sensing zone). If the object speed (i.e., the fluid speed at the center of the sensing cell) and the time duration of the negative-going pulse are known, the processor can calculate the length of the object (particularly valuable with elongated multicellular organisms).

Fluid speed can be maintained by precision mechanical design, or, less expensively, by seeding the fluid with a very low concentration of small polystyrene microspheres and then detecting the light extinction signal from these microspheres while the sample organisms are being counted. The organisms and microspheres can be made to have completely distinguishable light extinction signals that can be acted upon differently by the computational electronics, even if a sample objects and a microsphere pass through the sensing zone together. The introduced microsphere's time of flight is not used to regulate the fluid speed, which tends to be expensive and difficult, but only to change the computational parameters used to calculate the sample organism length. The biological effect of the plastic microspheres may be detrimental to certain species or to downstream processes, and should therefore be evaluated carefully before implementation.

If there is a good biological correlation between the length and diameter of the organism, the time-of-flight length measurement may yield sufficient size information. If this correlation does not exist in the population of interest and microspheres cannot be used, the organism's diameters can be measured by a second detector positioned off-axis in the x-direction. This detector will register an electronically positive-going, light-scatter pulse. The amplitude, as opposed to the duration, of the electronic pulse can be related in real time to the diameter of the sample organism via a set of light scattering equations stored in the computer system. The light extinction signal from the on-axis detector and the light scatter signal from the off-axis detector can be combined by the computer to give a real-time calculation of all dimensions of the sample organism. Of course, different types of organisms (e.g., nematodes versus fruit fly larvae) will require somewhat different prestored scattering information.

Referring to FIGS. 10A and 10B, the light scattering theory usually applied to objects in flow cytometry is termed Rayleigh-Gans, or anomalous diffraction, theory. It applies to objects that are large compared to the source wavelength and that exhibit a low refractive index relative to the surrounding medium, which is water in this case. Using this theoretical treatment as a first approximation, the processor can use the assumption that light blockage signals follow the area of geometric shadow for the sample organisms. In the case of nematodes the sample population may include adult worms, larvae, and eggs. Under this assumption, the temporal signal for an adult nematode and an egg together would appear as shown in FIG. 10A. Standard electronic methods can be applied to such a signal to distinguish between an adult nematode signal and one that is coincident with an egg. For example, computing the derivative of a blockage signal, as shown in FIG. 10B, allows an adult-egg coincidence to be more readily detected; for example, an odd number of pulses in a pulse train is indicative of a coincidence. It is noted that even though the nematodes are too large in diameter to be accurately handled by Rayleigh-Gans, or anomalous diffraction, theory, this treatment may be sufficient for many purposes. More detailed models could also be developed to obtain more information about the nematodes or other multicellular sample organisms. Overall, optical detection is particularly versatile in measuring the size and shape of sample organisms or other large objects.

Referring to FIGS. 8A, 8B, and 9, although the fluid design presented in FIG. 2 is inexpensive and easy to clean, other fluid designs also present advantages. In a first design alternative, the sheath vessel is pressurized, and the sample (nematode) flow is driven by a syringe pump 90 (see FIG. 7A). The cost of such a system is higher and clean-out may be more difficult, but this alternative exhibits greater flow stability which allows the flow velocity to be more tightly regulated, which may make microspheres unnecessary while providing more accurate size discrimination. The syringe barrel in this alternative design can be rotated to keep the sample organisms in suspension (see FIG. 7B.) This can be accomplished most readily by rolling the barrel back and forth (oscillatory rotation) because there is no need for a rotating fluid seal. A ribbed interior to the syringe barrel may also facilitate mixing.

In a second alternative approach, a syringe 92 is provided with a rigid sample (nematode) chamber 94 through a system of check valves 96, 98 (see FIG. 9). In this alternative system, sample organisms are not drawn actually into the syringe barrel, but are instead held in the rigid chamber 94. A sample organism-friendly fluid without organisms is drawn into the syringe periodically through the check valves and mixing takes place outside the syringe as the fluid enters the chamber 94 (which is equipped with mixers to keep the organisms in suspension. This alternative method of operation does not require syringe changes to replenish the organism supply. Both of these alternative approaches can use ordinary disposable plastic syringes.

The alternative designs may be less likely to produce significant pressure transients in the fluid lines. Such pressure transients could slow down or shut off sample flow in the flow cell all together and result in a period during which organisms are not centered and not oriented. In the fluidic system presented in FIG. 2, methods of stirring the organisms should be chosen to keep them in suspension without introducing significant pressure transients. Magnetic stirrers producing upwelling are available, and may be the simplest solution. A roller bottle or Archimedes screw configuration does not introduce fluidic noise and provides effective suspension of the sample organisms. The fluid lines in the storage vessel should not move during operation, and, for this reason, the flow cell should remain stationary while the plate moved to effect changes in container position. While very stable, the sample containers in the alternative embodiments must be ultimately refilled, which can result in down time for the system as compared to the device of FIG. 2 where the sample can rapidly be replenished.

Figure 12:
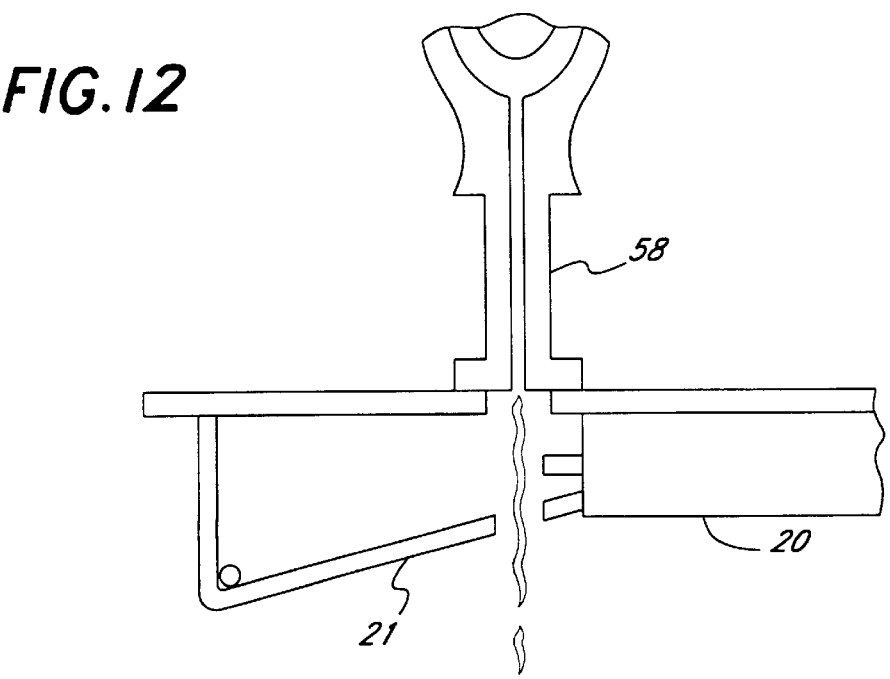
FIG. 12 is a diagrammatic cross-section of sections of an embodiment of the large object dispensing system of FIG. 1.

Referring now to FIG. 12, one embodiment of the sensing chamber 58 can be made of an upright quartz rectangular parallelepiped with a 250 $\mu$m diameter capillary passing through its longitudinal axis and defining a sensing zone. Note that although the square cross-section is preferred, it is also possible to use other sensing chamber geometries, or even to omit the sensing chamber walls altogether, leaving only an open sensing zone. The fluid output of the actuator 20 is preferably located less than about one centimeter below the outlet of the capillary and at about one millimeter from the undisturbed position of the liquid flow. It is important that the actuator 20 be located so as not to introduce fluidic instabilities into the flow stream. The one millimeter dimension has been found to be optimal for this embodiment, because it appears to result in atomization of the fluid rather than a deflection of the flow, which tends to result in flow disturbances. The actuating fluid flow direction is aimed substantially at right angles to the sample fluid flow.

Figure 13:
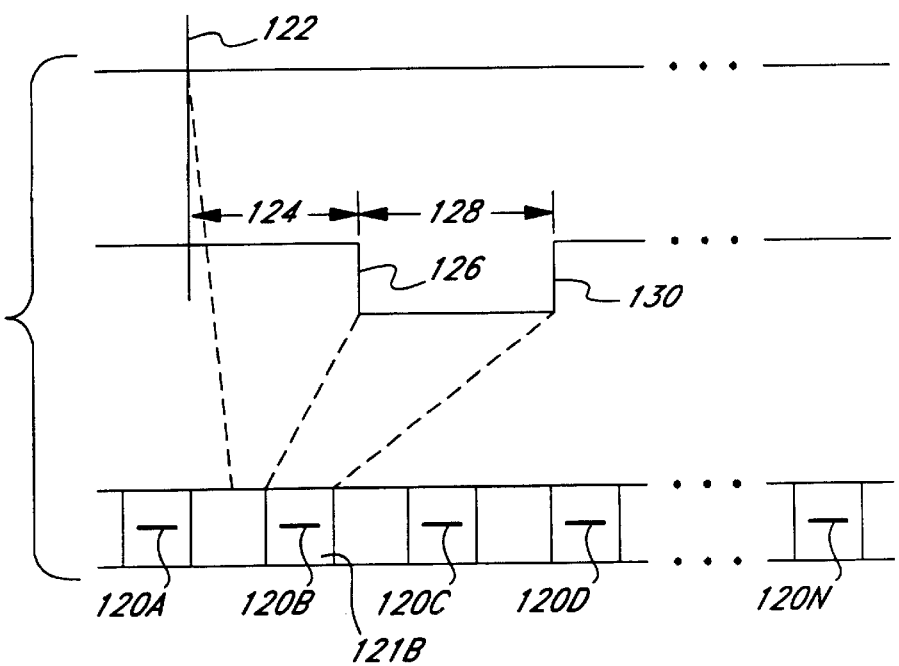
FIG. 13 is a diagram illustrating nematode flow over time and corresponding electronic signals for one nematode on a different scale, for the dispensing system portions of FIG. 12.

Referring to FIG. 13, the flow of sample organisms (here nematodes) 120A, 120B, . . . 120N over time tends to be irregular. Simply dispensing groups of them while leaving the actuator valve deactivated may result in different volumes of liquid being conveyed with different groups. For this reason, the valve is deactivated only when one of the nematodes is present. When a nematode (e.g., 120D) is detected in the capillary, a peak detect signal 122 is derived from the output of the detector. After a travel period 124 that is related to the travel time of the nematode from the detector beam to the actuator and to the response time of the actuator, the actuator is turned off (edge 128). The actuator is then kept off for a pass period 126, turned on (edge 130), and left on until a peak detect signal is detected for the next nematode. This timing allows the nematode and a predetermined amount of surrounding liquid 121B to pass into the vessel below, but prevents excess liquid from entering the vessel. In one embodiment the travel period is four microseconds, and the pass period is adjustable from four to ten microseconds. The system can also be programmed to pass more than one nematode in each pass period. Typically, the organism is encased in a cylindrical fluid segment that is several millimeters in length and approximately 0.2 millimeters in diameter. The volume of the fluid segment containing the organism is of the order of magnitude of one microliter or slightly less. Therefore, if only one or a few organisms is dispensed into each microwell, the dilution effect on a test sample of 50–100 microliters is negligible.

Ensuring that a only predetermined amount of liquid accompanies a population of sample organisms is beneficial for several reasons. It may be difficult to accurately meter similar doses of test substances into different containers if there are different amounts of liquid in each of the containers. Longevity and activity of the sample organisms may also be affected, since increasing the amount of liquid in each container increases the volume-to-surface area ratio for the container, which can affect oxygen uptake for the sample organism. Making large, single, elongate droplets that each contain a single sample organism also helps to avoid injury to the organism as it is dispensed.

Other methods may also be suitable for diverting the fluid flow. Such methods may include the use of electrostatic, piezoelectric, ferrofluidic, or other suitable fluid switches. In order to keep the sample organisms alive, however, these methods must be carefully tailored. For example, experiments with electrostatic switching arrangements appear to indicate that exposing multicellular organisms such as nematodes to high frequency mechanical vibrations used to break-the flow stream into variably charged droplets and to the high intensity electric fields used to deflect those droplets is frequently lethal to the organisms. As a result, the electric field levels and vibration levels for this type of switch would have to be reduced at the expense of other system parameters to act as a suitable switch for multicellular organisms. Even then the analysis presented above indicates that the great fall distances required for adequate deflection of large (e.g., greater than about 50 $\mu$m) droplets essentially precludes the use of electrostatic sorting methods with large objects. Ferrofluidic additives may also prove detrimental to the sample organisms or interact with agents to be tested on the organisms, so the effect of any such additive must be carefully evaluated before its selection. Further, the addition of a ferrofluidic material adds to expense and experimental complexity. Piezoelectric valves, such as those presented in "A New Fluid Switching Flow Sorter," by J. Duhnen et al., Histochemistry 77:117, (1983), introduce substantial shock waves into the fluid and may therefore also result in injury to multicellular organisms. The transducer's mechanical output level, the geometry of the sorter, and the switching margin must therefore be adjusted to suit the population to be sorted. For the reasons discussed above, the use of a fluid valve is presently contemplated to be the most appropriate approach to diverting the fluid flow for multicellular organisms. Again, it is important that the fluid valve be physically isolated from the flow orientation and detection systems to avoid introducing fluidic instabilities that would impair orientation and detection. In many of the described examples the diverting fluid is a gas, namely air. It is clear that other gases such as nitrogen or argon can be readily substituted for air. It is also contemplated that other fluids such as liquids may be used in the present invention.

Other types of objects can be sorted using techniques described in this application, elongate, multicellular animals are of particular interest. For example, live fruit fly larvae (*Drosophila melanogaster*) have been successfully dispensed using these techniques. It is also believed that these techniques are well suited to dispensing and sorting the elongate embryos of zebrafish (*Danio rerio*). Obviously other multicellular organisms of similar sizes such as additional nematode or other worms, insect larvae, other arthropod or molluscan or vertebrate larvae are equally useable in the present invention. Nor should embryos of various plants be overlooked for testing compounds of agricultural rather than pharmaceutical use. Apart from multicellular organisms, large microspheres used in combinatorial chemistry to produce libraries of test compounds are preferred objects to be analyzed and deposited by the instrument of the present invention.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. An instrument for analyzing and selectively dispensing sample objects greater than about 50 $\mu$m in diameter encapsulated in a continuous liquid sample stream in air, the instrument comprising:

a sample object source containing sample objects greater than about 50 µm in diameter in a fluid suspension, said source having an output opening;

an alignment chamber having an input opening in fluidic communication with the output opening of the sample object source and having an output opening;

a sample object sensing zone having an input opening in fluidic communication with the output opening of the alignment chamber, said object sensing zone having an output opening which produces a continuous liquid stream in air;

a sample detector responsive to presence of sample objects in the sensing zone; and a fluid switch downstream of the output of the sample object sensing zone, said fluid switch controlling a fluid stream intersecting the continuous liquid stream in air for disrupting said stream such disrupting physically isolated from the sample object sensing zone and the alignment chamber to prevent introduction of fluidic instabilities therein, said switch responsive to the sample detector to turn off intermittently said intersecting fluid stream thereby allowing lengths of the continuous liquid sample stream in air containing detected objects to pass undisrupted to a sample container.

2. The instrument of claim 1, wherein the fluid switch comprises a source of compressed gas and an electrically operated valve to interrupt a gas stream from the source of compressed gas.

3. The instrument of claim 2, wherein the fluid switch is operative to interact with the sample stream with sufficient force to convert said stream into a spray of droplets.

4. The instrument of claim 1, wherein the fluid switch is responsive to a delayed detection signal from the sample detector.

5. The instrument of claim 1, wherein the fluid switch is operative to include only predetermined amounts of fluid with detected objects passing to the sample container.

6. The instrument of claim 1 further comprising a controller connected between the sample detector and the fluid switch and operative to cause said switch to select one sample object at a time.

7. The instrument of claim 1, wherein the alignment chamber has an input opening for a sheath fluid.

8. The instrument of claim 7, wherein a relationship between the alignment chamber and the output of the sample source is defined to maintain a Reynolds number of about one hundred or less between said output opening and a volume of the sensing zone.

9. The instrument of claim 1 further comprising an illumination source directed toward the sensing zone, and wherein the sample detector is an optical detector.

10. The instrument of claim 9 further comprising a processor operative to determine the length of at least one of the sample objects by measuring the time that the at least one of the sample objects takes to pass between the detector and the illumination source.

11. The instrument of claim 9 further comprising an off-axis detector, located across the sensing zone along an illumination axis of the illumination source.

12. The instrument of claim 11, wherein the off- axis detector is generally perpendicular t o an illumination axis of the illumination source.

13. The instrument of claim 9, wherein the illumination source is a focused low-power laser.

14. The instrument of claim 9, wherein the sensing zone has a height of about 10–40 μm.

15. The instrument of claim 9, wherein the sensing zone is defined by a set of walls having a square cross-section.

16. The instrument of claim 1, wherein the output of the sample object source is separated from the sensing zone by a total conduit volume of less than 500 microliters.

17. An instrument for analyzing and selectively dispensing sample objects greater than about 50 μm in diameter encapsulated in a continuous liquid sample stream in air, the instrument comprising:

means for aligning the sample objects in a fluid stream, in a direction parallel to a flow direction of the fluid stream;

means for detecting the presence of the sample objects in the fluid stream, the means for detecting being located downstream from the means for aligning with respect to the fluid stream;

means for forming a continuous liquid sample stream in air; and means for selectively disrupting the continuous liquid sample stream in air, the means for selectively disrupting located downstream from the means for detecting with respect to the fluid stream, such disrupting being physically isolated from said means for detecting so that fluidic instabilities cannot be transmitted from the means for selectively disrupting to the means for detecting, and being responsive to the means for detecting so as intermittently to cease disrupting the continuous fluid stream in air thereby allowing undisrupted lengths of said stream in air containing sample objects to pass undisturbed into a container.

18. The instrument of claim 17, wherein the means for selectively disrupting includes only a predetermined amount of fluid with each sample object.

19. An instrument for analyzing and selectively dispensing sample objects encapsulated in a continuous liquid sample stream in air, the instrument comprising:

a source of objects having an output;

a sensing zone responsive to sample objects from the output;

a detector responsive to sample objects in the sensing zone;

means for forming a continuous liquid sample stream in air; and a switched source of compressed gas having a gas output directed toward the continuous liquid sample stream in air downstream from the detector so as to disrupt said stream, such disruption physically isolated from the detector to prevent transmissions of fluidic instabilities to the detector, and having a control input responsive to the detector to cease disrupting said stream thereby allowing lengths of the liquid sample stream containing detected objects to pass undisrupted to a sample container.

20. The instrument of claim 19, wherein the switched source of compressed gas includes a source of compressed gas and an electrically operated valve to interrupt a gas stream from the source of compressed gas.

21. The instrument of claim 19, wherein the switched source of compressed gas is operative to interact with a fluid stream from the detector with sufficient force to convert the fluid stream into a spray of droplets.

22. The instrument of claim 19, wherein the switched source of compressed gas is responsive to a delayed detection signal from the detector.

23. The instrument of claim 19, wherein the switched source is operative to repeatedly leave predetermined amounts of fluid undisrupted.

24. The instrument of claim 19, further comprising a second switched source of compressed gas positioned to disrupt fluid left undisrupted by the switched source of compressed gas.

25. The instrument of claim 19, wherein the source of objects is a source of elongate, multicellular animals.

26. An instrument for selectively dispensing sample objects encapsulated in a continuous liquid sample stream in air, the instrument comprising:
   means for providing a fluid stream carrying sample objects;
   means for detecting the presence of the sample objects in the fluid stream, the means for detecting being located downstream from the means for providing with respect to the fluid stream;
   means for forming a continuous liquid sample stream in air; and
   means for selectively directing a gas stream toward the fluid stream to disrupt portions of the continuous sample stream in air, the means for selectively directing being located downstream from the means for detecting with respect to the fluid stream, physically isolating sample stream in air disruption from the means for detecting so as not to introduce fluidic instabilities to the means for detecting, and being responsive to the means for detecting intermittently to cease sample stream in air disruption thereby allowing lengths of the continuous liquid sample stream in air containing detected objects to pass undisrupted to a sample container.

27. The instrument of claim 26, wherein the means for selectively directing operates so as to include only a predetermined amount of the continuous sample stream in air with each of the detected objects.

28. The instrument of claim 26, wherein the means for providing provides live elongate, multicellular animals as the objects, and wherein the means for selectively directing is operative to select said animals while leaving viability of the animals unimpaired.

29. A method of dispensing sample objects encapsulated in a continuous liquid sample stream in air comprising the steps of:
   centering and orienting the sample objects in a flowing fluid stream;
   passing the fluid stream through a sensing zone with a surrounding sheath fluid;
   detecting the presence of the sample objects in the sensing zone;
   forming the fluid stream into a continuous liquid sample stream in air;
   diverting at least some portion of the sample stream in air with a switched fluid stream , wherein said diverting is physically isolated from the sensing zone so as to not induce fluidic instabilities therein; and
   collecting ones of the sample objects by intermittently ceasing to divert at least some portion of the sample stream in air based on the step of detecting so that remaining portions of the sample stream are not diverted by the step of diverting are collected.

30. The method of claim 29, wherein the step of diverting includes a step of converting the sample stream in air into a spray of droplets.

31. The method of claim 29, wherein the step of collecting takes place for a predetermined period of time for each of the sample objects detected in the sample zone.

32. The method of claim 29 further comprising a step of illuminating the sensing zone, and wherein the step of detecting detects light from the step of illuminating.

33. The method of claim 29, wherein the step of detecting employs an on-axis detector and an off-axis detector and combines signals from these detectors.

34. The method of claim 29, wherein the step of centering includes a step of conveying a sheath fluid past a nozzle.

35. The method of claim 34, wherein the step of conveying is performed with a maximum Reynolds number of around one hundred.

36. The method of claim 29 further comprising a step of sorting the sample objects into a plurality of categories wherein the step of collecting collects the categories in a plurality of different containers.

37. The method of claim 29, wherein the sample objects are multicellular organisms and further comprising the step of exposing the multicellular organisms collected in the step of collecting to a pharmaceutical agent.

38. The method of claim 29, wherein the step of collecting the sample objects further includes dispensing predetermined numbers of sample objects into each of a plurality of containers.

39. The method of claim 29, wherein the step of centering includes reference particles with the sample objects.

40. The method of claim 29, wherein the step of collecting includes dispensing only sample objects having a predetermined characteristic into a container.

41. An instrument for analyzing and selectively dispensing sample objects encapsulated in a continuous liquid sample stream in air, the instrument comprising:
   a sample source containing sample objects in a fluid suspension for dispensing a fluid suspension of sample objects;
   an alignment chamber having an input in fluidic communication with an output of the sample source for aligning a longitudinal axis of the sample sources with a direction of flow of the fluid suspension;
   a sample object sensing zone having an input in fluidic communication with an output of the alignment chamber;
   a sample detector for detecting sample objects in the sensing zone;
   an orifice downstream from the sensing zone for producing a continuous sample stream in air from the fluid suspension; and
   a fluid switch downstream of the orifice, said fluid switch controlling a fluid stream intersecting the continuous liquid stream in air for disrupting said stream, such disrupting physically isolated from the sample object sensing zone and the alignment chamber to prevent introduction of fluidic instabilities therein, said switch responsive to the sample detector to turn off intermittently said intersecting fluid stream thereby allowing lengths of the continuous liquid sample stream in air containing detected objects to pass undisrupted to a sample container.

42. The instrument of claim 41, wherein the fluid switch comprises a source of compressed gas and an electrically operated valve to interrupt a gas stream from the source of compressed gas.

43. The instrument of claim 42, wherein the fluid switch is operative to interact with the sample stream with sufficient force to convert said stream into a spray of droplets.

44. The instrument of claim 41, wherein the fluid switch is responsive to a delayed detection signal from the sample detector.

45. The instrument of claim 41, wherein the fluid switch is operative to include only predetermined amounts of fluid with detected objects passing to the sample container.

46. The instrument of claim 41 further comprising a controller connected between the sample detector and the fluid switch operative to cause said switch to pass one sample object at a time.

47. The instrument of claim 41, wherein the alignment chamber has an input for a sheath fluid.

48. The instrument of claim 47, wherein a relationship between the sample object sensing zone and the output of the sample source is defined to maintain a Reynolds number of about one hundred or less between said output and a volume of the sensing zone.

49. The instrument of claim 41 further comprising an illumination source directed toward the sensing zone, and wherein the sample detector is an optical detector.

50. The instrument of claim 49 further comprising a processor operative to determine the length of at least one of the sample objects by measuring the time that the at least one of the sample objects takes to pass between the detector and the illumination source.

51. The instrument of claim 49 further comprising an off-axis detector, located across the sensing zone along an illumination axis of the illumination source.

52. The instrument of claim 51, wherein the off-axis detector is generally perpendicular to an illumination axis of the illumination source.

53. The instrument of claim 49, wherein the illumination source is a focused low-power laser.

54. The instrument of claim 49, wherein the sensing zone has a height of about 10–40 $\mu$m.

55. The instrument of claim 49, wherein the sensing zone is defined by a set of walls having a square cross-section.

56. The instrument of claim 41, wherein the output of the sample object source is separated from the sensing zone by a total conduit volume of less than 500 microliters.

* * * * *